US009492660B2

(12) United States Patent
Mouchawar et al.

(10) Patent No.: US 9,492,660 B2
(45) Date of Patent: Nov. 15, 2016

(54) IMPLANTABLE NEUROSTIMULATION SYSTEMS AND METHODS THEREOF (71) Applicant: PACESETTER, INC., Sylmar, CA (US)

(72) Inventors: Gabriel A. Mouchawar, Valencia, CA (US); Gary R. Dulak, Moorpark, CA (US); Richard Williamson, Santa Monica, CA (US); Reza Shahandeh, Thousand Oaks, CA (US); Xiaoyi Min, Camarillo, CA (US); Shiloh Sison, Alameda, CA (US); Aaron Raines, Dallas, TX (US); DeLea Peichel, Carrollton, TX (US)

(73) Assignee: PACESETTER, INC., Sylmar, CA (US)

( * ) Notice: Subject to any disclaimer, the term of this patent is extended or adjusted under 35 U.S.C. 154(b) by 114 days.

(21) Appl. No.: 14/565,155

(22) Filed: Dec. 9, 2014

(65) Prior Publication Data

US 2016/0158540 A1    Jun. 9, 2016

(51) Int. Cl.
*A61N 1/00* (2006.01)
*A61N 1/08* (2006.01)
*A61N 1/05* (2006.01)
*A61N 1/36* (2006.01)

(52) U.S. Cl.
CPC .............. *A61N 1/08* (2013.01); *A61N 1/0534* (2013.01); *A61N 1/0539* (2013.01); *A61N 1/36067* (2013.01); *A61N 1/36082* (2013.01); *A61N 2001/086* (2013.01)

(58) Field of Classification Search
CPC .......................... A61N 1/0534; A61N 1/0539
USPC ......................................................... 607/116
See application file for complete search history.

(56) References Cited

U.S. PATENT DOCUMENTS

| | | | |
|---|---|---|---|
| 7,212,110 B1 | 5/2007 | Martin et al. | |
| 7,228,179 B2 | 6/2007 | Campen et al. | |
| 7,571,007 B2 | 8/2009 | Erickson et al. | |
| 7,747,318 B2 | 6/2010 | John et al. | |
| 8,140,152 B2 | 3/2012 | John et al. | |
| 8,509,876 B2 | 8/2013 | Karmarkar | |
| 8,718,777 B2 | 5/2014 | Lowry et al. | |
| 2005/0075680 A1 | 4/2005 | Lowry et al. | |
| 2006/0170486 A1 | 8/2006 | Tranchina et al. | |
| 2007/0233158 A1* | 10/2007 | Rodriguez | A61N 1/0539 606/130 |
| 2008/0140149 A1 | 6/2008 | John et al. | |
| 2009/0118804 A1* | 5/2009 | Moffitt | A61B 5/6864 607/116 |
| 2009/0292344 A1 | 11/2009 | Lowry et al. | |

(Continued)

FOREIGN PATENT DOCUMENTS

WO        2001093953 A1    12/2001

*Primary Examiner* — Amanda Patton
*Assistant Examiner* — Philip C Edwards (57) ABSTRACT The present disclosure provides neurostimulation methods and system for deep brain stimulation. A neurostimulation system for deep brain stimulation includes a burr hole plug including a cover and a base, and at least one deep brain stimulation (DBS) lead extending through an aperture defined through the base, the at least one DBS lead including at least one DBS electrode configured to apply stimulation to a subject. The system further includes an implantable pulse generator (IPG), an extension electrically coupling the IPG to the at least one DBS lead, and an indifferent electrode positioned proximate the at least one DBS electrode to facilitate reducing an area between the indifferent electrode and the at least one DBS electrode.

11 Claims, 6 Drawing Sheets

(56) References Cited

U.S. PATENT DOCUMENTS

| | | | |
|---|---|---|---|
| 2010/0114281 A1* | 5/2010 | Swoyer | A61N 1/0534 607/116 |
| 2010/0217341 A1 | 8/2010 | John et al. | |
| 2011/0072657 A1 | 3/2011 | Swanson et al. | |
| 2014/0194720 A1 | 7/2014 | Hua | |

* cited by examiner

IMPLANTABLE NEUROSTIMULATION SYSTEMS AND METHODS THEREOF

FIELD OF THE DISCLOSURE

The present disclosure relates generally to neurostimulation methods, systems, and more particularly to a neurostimulation system for deep brain stimulation that facilitates mitigating unintended current flow due to magnetic flux.

BACKGROUND ART

Neurostimulation is a treatment method utilized for managing the disabilities associated with pain, movement disorders such as Parkinson's Disease (PD), dystonia, and essential tremor, and also a number of psychological disorders such as depression, mood, anxiety, addiction, and obsessive compulsive disorders. Deep brain stimulation systems deliver stimulation to a patient's brain.

At least some known deep brain stimulation (DBS) systems include a plug that mounts to a burr hole formed in the patient's skull. A lead including stimulation electrodes is coupled to the plug. The plug includes mechanical features (e.g., a clamping mechanism) that lock the lead in place over an exit point from the patient's brain. The lead exits the brain, and is coupled to a stimulation device (e.g., an implantable pulse generator) via an extension. The stimulation device may be located, for example, in the patient's chest.

Figure 1:
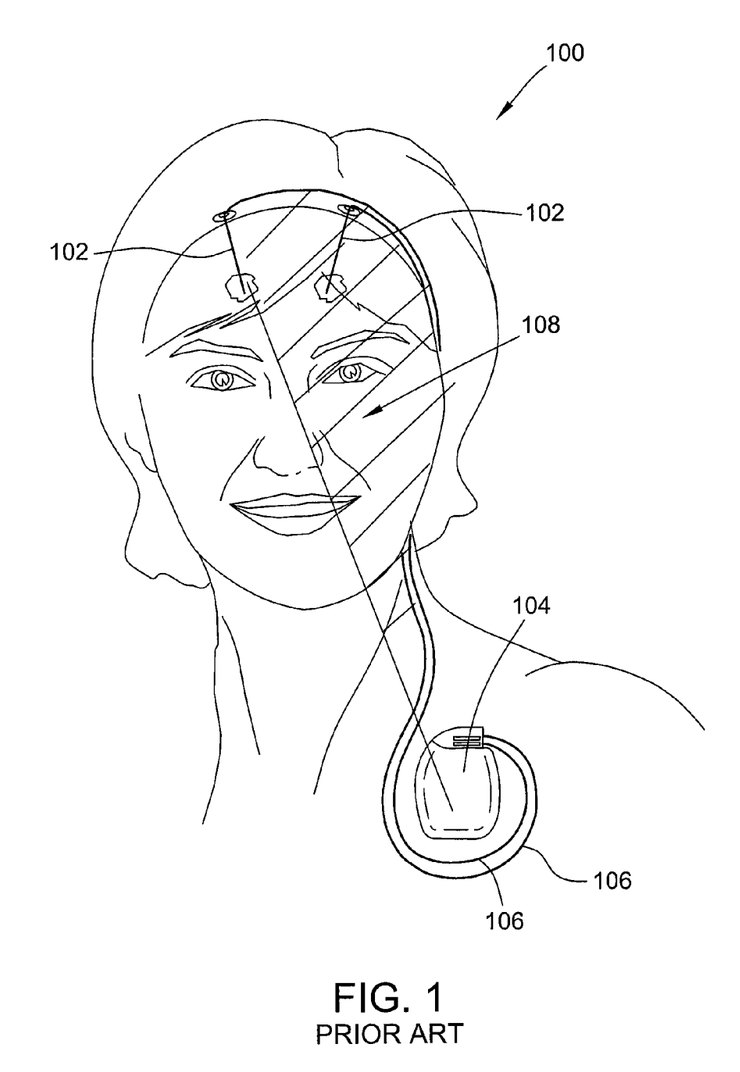
FIG. 1 is a schematic view of a known deep brain stimulation system.

For example, FIG. 1 is a schematic view of a known deep brain stimulation system 100. System 100 includes a plurality of DBS leads 102 electrically coupled to a stimulation device 104 using associated extensions 106. As indicated by a region 108, when stimulation device 104 functions as an indifferent electrode for DBS leads 102 in a unipolar configuration, DBS leads 102 and stimulation device 104 form a relatively large current loop. During magnetic resonance imaging (MRI) scans, magnetic flux through the current loop due to MRI gradient fields can generate unintended current flow through extension 104 and/or DBS leads 102. This unintended current flow may result in electrical stimulation being applied by DBS leads 102 that exceeds target stimulation thresholds.

BRIEF SUMMARY OF THE DISCLOSURE

In one embodiment, the present disclosure is directed to a neurostimulation system for deep brain stimulation. The neurostimulation system includes a burr hole plug including a cover and a base, and at least one deep brain stimulation (DBS) lead extending through an aperture defined through the base, the at least one DBS lead including at least one DBS electrode configured to apply stimulation to a subject. The system further includes an implantable pulse generator (IPG), an extension electrically coupling the IPG to the at least one DBS lead, and an indifferent electrode positioned proximate the at least one DBS electrode to facilitate reducing an area between the indifferent electrode and the at least one DBS electrode.

In another embodiment, the present disclosure is directed to a burr hole plug for use with a neurostimulation system for deep brain stimulation. The burr hole plug includes a cover, and a base selectively coupleable to the cover, the base including an aperture defined therethrough, and a metallic bottom configured to function as an indifferent electrode for a deep brain stimulation (DBS) lead that passes through the aperture.

In another embodiment, the present disclosure is directed to a method for implanting a neurostimulation system for deep brain stimulation. The method includes inserting at least one deep brain stimulation (DBS) lead into a brain of a subject, the at least one DBS lead including at least one electrode configured to apply stimulation to the subject, mounting a burr hole plug to a skull of the subject such that the at least one DBS lead extends through an aperture defined through the burr hole plug, the burr hole plug including a cover and a base, electrically coupling the at least one DBS lead to an implantable pulse generator (IPG) using an extension, and positioning an indifferent electrode proximate the at least one DBS lead.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The systems and methods described herein facilitate mitigating unintended current flow due to magnetic flux. A neurostimulation system for deep brain stimulation includes a burr hole plug including a cover and a base, at least one deep brain stimulation (DBS) lead extending through an aperture defined through the base, the at least one DBS lead including at least one DBS electrode configured to apply stimulation to a subject, an implantable pulse generator (IPG), an extension electrically coupling the IPG to the at least one DBS lead, and an indifferent electrode positioned proximate the at least one DBS electrode to facilitate reducing an area between the indifferent electrode and the at least one DBS electrode. By locating the indifferent electrode proximate the at least one DBS lead/electrode, the likelihood of unintended current flow being generated by magnetic flux is significantly reduced.

Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Peripheral nerve field stimulation (PNFS) is another form of neuromodulation. The basic devices employed for PNFS are similar to the devices employed for SCS including pulse generators and stimulation leads. In PNFS, the stimulation leads are placed in subcutaneous tissue (hypodermis) in the area in which the patient experiences pain. Electrical stimulation is applied to nerve fibers in the painful area. PNFS has been suggested as a therapy for a variety of conditions such as migraine, occipital neuralgia, trigeminal neuralgia, lower back pain, chronic abdominal pain, chronic pain in the extremities, and other conditions.

Figure 2:
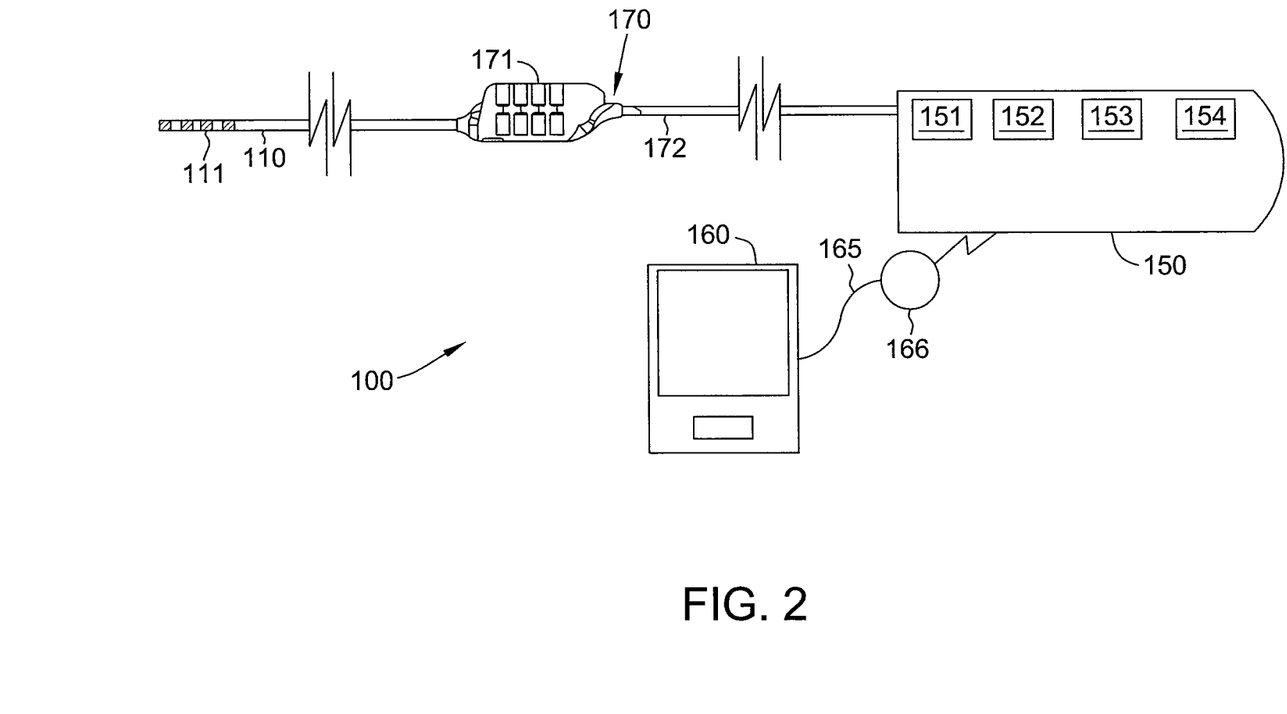
FIG. 2 is a schematic view of one embodiment of a stimulation system.

Referring now to the drawings, and in particular to FIG. 2, a stimulation system is indicated generally at 100. Stimulation system 100 generates electrical pulses for application to tissue of a patient, or subject, according to one embodiment. System 100 includes an implantable pulse generator 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of pulse generator 150 for execution by the microcontroller or processor to control the various components of the device.

Pulse generator 150 may comprise one or more attached extension components 170 or be connected to one or more separate extension components 170. Alternatively, one or more stimulation leads 110 may be connected directly to pulse generator 150. Within pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from pulse generator 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 3A:
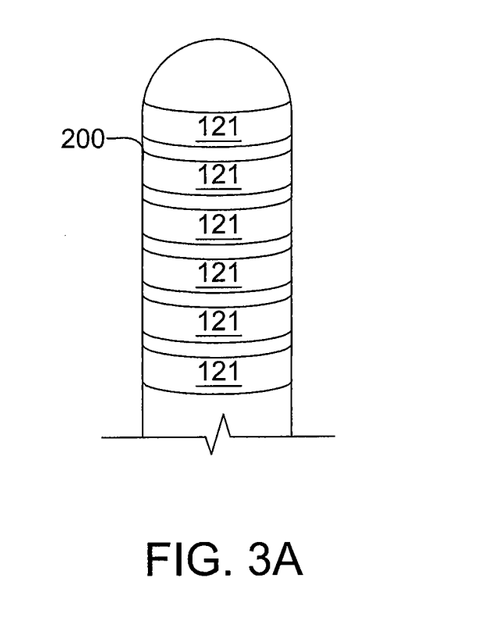
FIGS. 3A-3C are schematic views of stimulation portions that may be used with stimulation system of FIG. 1.
Figure 3B:
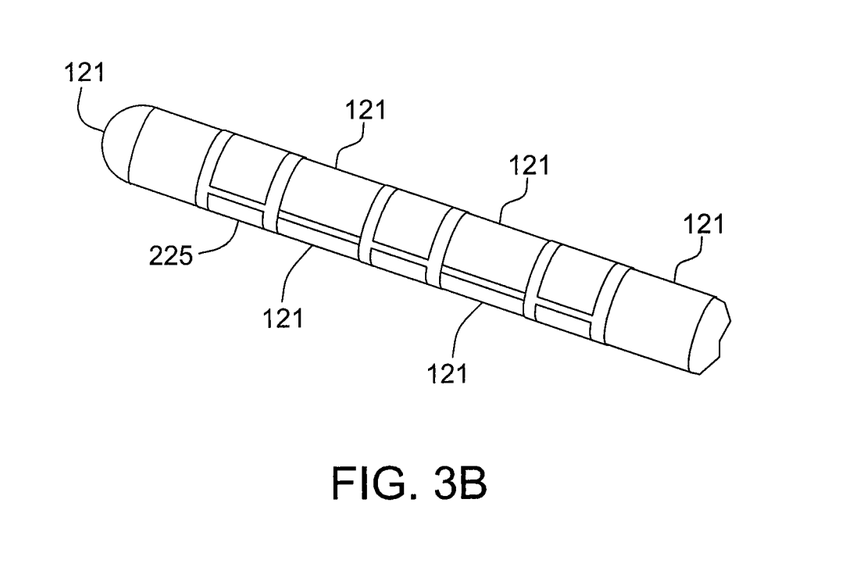
Figure 3C:
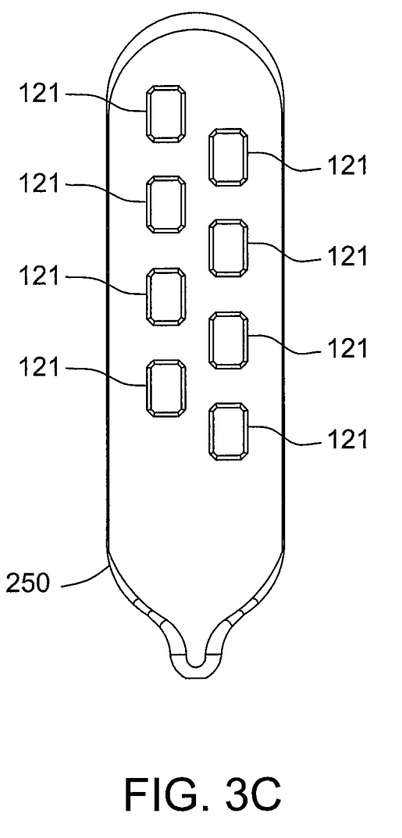

FIGS. 3A-3C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Controller device 160 may be implemented to recharge battery 153 of pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of generator 150. The charging circuitry may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 150 to be controlled by user after pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Example commercially available neurostimulation systems include the EON MINI™ pulse generator and RAPID PROGRAMMER™ device from St. Jude Medical, Inc. (Plano, Tex.). Example commercially available stimulation leads include the QUATTRODE™, OCTRODE™, AXXESS™, LAMITRODE™, TRIPOLE™, EXCLAIM™, and PENTA™ stimulation leads from St. Jude Medical, Inc.

Figure 4:
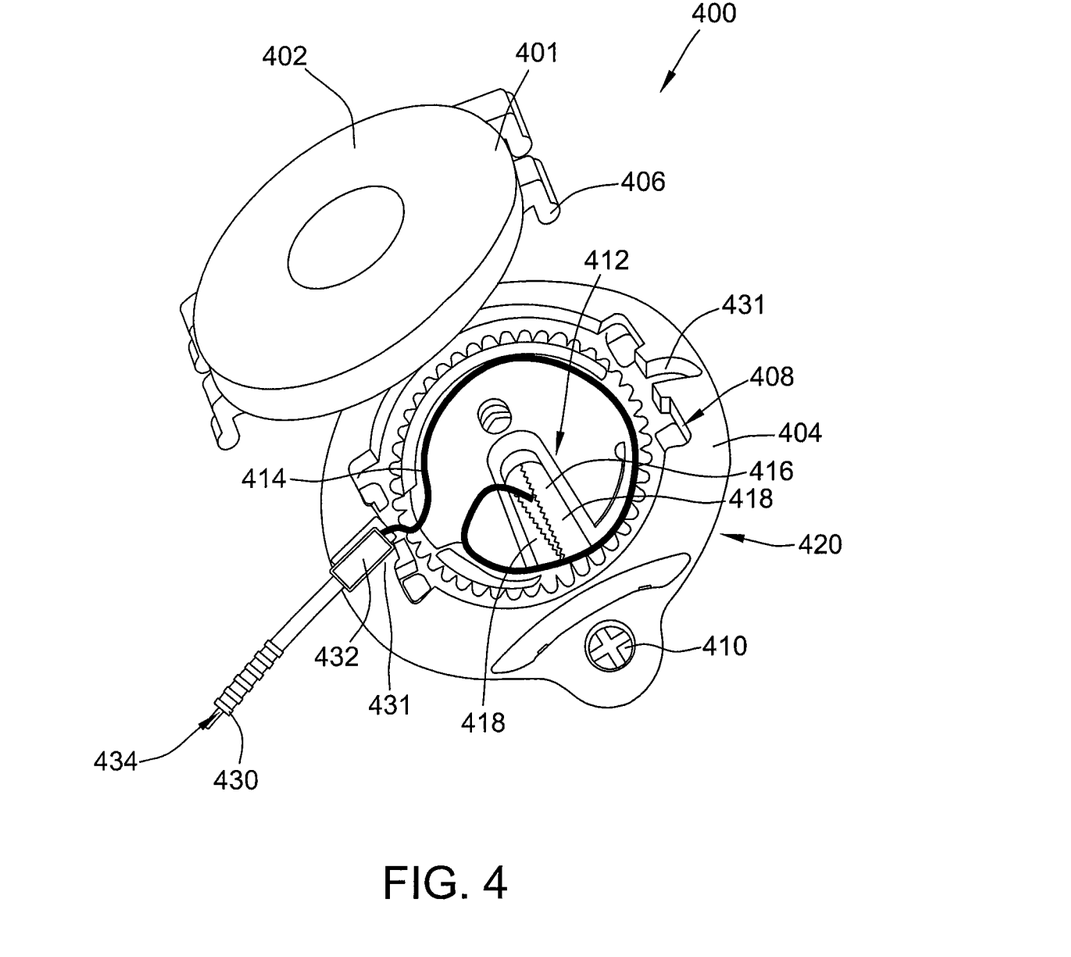
FIG. 4 is a perspective view of one embodiment of a deep brain stimulation system.

In FIG. 4, an implantable neurostimulation system for deep brain stimulation (DBS) is indicated generally at 400. Neurostimulation system 400 includes a burr hole plug 401 including a cover 402 and a base 404. Cover 402 is selectively coupleable to base 404. In the illustrated embodiment, cover 402 includes a plurality of prongs 406 that engage corresponding slots 408 defined in base 404 for a snap-fit engagement between cover 402 and base 404. Alternatively, cover 402 and base 404 may be coupled to one another using any suitable mechanism.

Base 404 is sized and shaped to insert into a burr hole (not shown) formed in the skull of a patient, or subject. One or more fasteners 410 (e.g., screws) facilitate securing base 404 to the skull. An elongated slot 412 is defined through base 404. A DBS lead 414 of neurostimulation system 400 extends through elongated slot 412, and a distal end of DBS lead 414 includes at least one stimulation electrode (not shown) implanted in the subject's brain. DBS lead 414 is electrically coupled to an implantable pulse generator (IPG), such as IPG 150 (shown in FIG. 2), via an extension (not shown in FIG. 4).

As shown in FIG. 4, elongated slot includes a clip 416 that facilitates securing DBS lead 414. Specifically, a portion of DBS lead 414 is sandwiched between opposing arms 418 of clip 416 such that clip 416 prevents DBS lead 414 from moving relative to base 404.

In at least some DBS systems, a stimulation device located in the subject's chest is utilized as an indifferent electrode for DBS leads implanted in the subject's brain. However, as explained above, this may result in unintended electrical stimulation when the subject undergoes magnetic resonance imaging (MRI). In contrast, in the systems and methods described herein, to facilitate reducing unintended electrical stimulation, an indifferent electrode is located proximate one or more DBS leads, as described in detail herein. The indifferent electrode may be designed to facilitate preventing heating in the presence of radio frequency (RF) fields from an MRI scanner. For example, the indifferent electrode may be relatively large and may be without relatively sharp edges.

In the embodiment shown in FIG. 4, a bottom 420 of base 414 forms the indifferent electrode. Specifically, bottom 420 is metallic (e.g., platinum, platinum-iridium, titanium, etc.). In some embodiments, the entire base 404 is metallic. Bottom 420 may be, for example, approximately 30 millimeters (mm) in diameter, corresponding to an area of approximately 707 mm$^2$. Further, DBS electrodes at a distal end of DBS lead 414, such as electrodes 111 and 121 (shown in FIGS. 2-3C), may have a surface area of approximately 6.08 mm$^2$. Accordingly, an area of bottom 420 may be significantly larger than an area of the DBS electrodes, substantially eliminating anodal stimulation from an indifferent electrode. To facilitate utilizing bottom 420 as the indifferent electrode, in some embodiments, the IPG may be coated with Parylene to close an indifferent electrode path between DBS lead 414 and the IPG.

In the illustrated embodiment, base 404 includes two metallic clips 431. Metallic clips 431 are electrically coupled to metallic bottom 420. To electrically coupled DBS lead 414 to bottom 420, an indifferent ring 432 on DBS lead 414 engages one of metallic clips 431. In one embodiment, indifferent ring 432 engages metallic clip 431 in a snap-fit engagement. Alternatively, indifferent ring 432 may engage metallic clip 431 in any configuration that electrically couples DBS lead 414 to bottom 420. As shown in FIG. 4, indifferent ring 432 has a fixed spacing to a proximal end 434 of DBS lead 414. Proximal end 434 includes an additional connector pin 430.

In the configuration of neurostimulation apparatus 400, any "current loop" susceptible to magnetic flux is relatively small. Specifically, any area susceptible to magnetic flux is formed by the portion of DBS lead 414 extending between the stimulation electrode at the distal end of DBS lead 414 and indifferent ring 432, which is electrically coupled to bottom 420. Since this portion of DBS lead 414 is substantially straight, the area formed is substantially zero and negligible amounts of current will be generated in DBS lead 414 in response to a magnetic flux.

Figure 5:
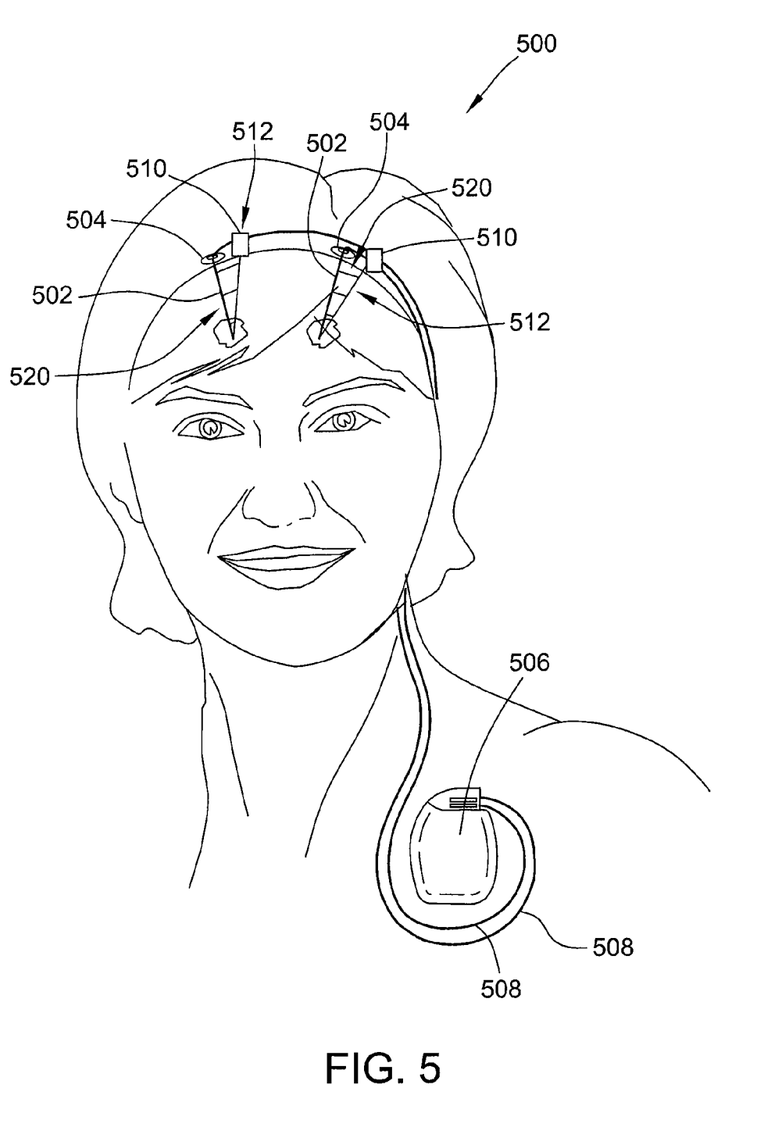
FIG. 5 is a schematic view of an alternative embodiment of a deep brain stimulation system.

FIG. 5 is a schematic diagram of an alternative neurostimulation system 500. In the illustrated embodiment, neurostimulation system 500 includes two DBS leads 502 each extending through respective burr hole plugs 504. Each DBS lead 502 is electrically coupled to an IPG 506 using an extension 508. In contrast to neurostimulation system 400, in neurostimulation system 500, indifferent electrodes 510 are located at an extension connection 512 between each DBS lead 502 and an associated extension 508.

In the illustrated embodiment, each indifferent electrode 510 is located approximately 2-5 centimeters (cm) away from an associated burr hole plug 504. Accordingly, regions 520 susceptible to magnetic flux are relatively small as compared to region 108 (shown in FIG. 1). Further, the surface area of indifferent electrodes 510 is smaller than the surface area of bottom 420 (shown in FIG. 4). To facilitate utilizing indifferent electrodes 510 as the return grounds, in some embodiments, IPG 506 may be coated with Parylene to close a return ground path between DBS leads 502 and IPG 506.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A neurostimulation system for deep brain stimulation, the neurostimulation system comprising:
a burr hole plug comprising a cover and a base;
at least one deep brain stimulation (DBS) lead extending through an aperture defined through the base, the at least one DBS lead including at least one DBS electrode configured to apply stimulation to a subject;
an implantable pulse generator (IPG);
an extension electrically coupling the IPG to the at least one DBS lead; and
an indifferent electrode positioned proximate the at least one DBS electrode to facilitate reducing an area between the indifferent electrode and the at least one DBS electrode;
the base including a metallic bottom, the metallic bottom comprising the indifferent electrode, with the indifferent electrode being sized and shaped to facilitate preventing heating during application of radio frequency fields; and
the at least one DBS lead including an indifferent ring and the base including at least one metallic clip with the metallic clip being configured to engage the indifferent ring such that the indifferent ring is electrically coupled to the metallic bottom.

2. The neurostimulation system of claim 1, wherein the at least one metallic clip is configured to engage the indifferent ring in a snap-fit engagement.

3. The neurostimulation system of claim 1, wherein the at least one DBS lead further comprises a connector pin positioned a fixed distance from the indifferent ring.

4. The neurostimulation system of claim 1, wherein the IPG is coated with Parylene.

5. The neurostimulation system of claim 1, wherein the indifferent electrode comprises a connector pin positioned at an extension connection between the at least one DBS lead and the extension.

6. A neurostimulation system for deep brain stimulation, the neurostimulation system comprising:

a burr hole plug comprising a cover and a base;
at least one deep brain stimulation (DBS) lead extending through an aperture defined through the base, the at least one DBS lead including at least one DBS electrode configured to apply stimulation to a subject;
an implantable pulse generator (IPG);
an extension electrically coupling the IPG to the at least one DBS lead;
an indifferent electrode positioned proximate the at least one DBS electrode to facilitate reducing an area between the indifferent electrode and the at least one DBS electrode;
the base including a metallic bottom, the metallic bottom comprising the indifferent electrode, with the indifferent electrode being sized and shaped to facilitate preventing heating during application of radio frequency fields;
the at least one DBS lead including an indifferent ring and the base including at least one metallic clip with the metallic clip being configured to engage the indifferent ring such that the indifferent ring is electrically coupled to the metallic bottom, wherein the at least one metallic clip being configured to engage the indifferent ring in a snap-fit engagement; and
the indifferent electrode including a connector pin positioned at an extension connection between the at least one DBS lead and the extension.

7. The neurostimulation system of claim 6, wherein the connector pin is positioned a fixed distance from the indifferent ring.

8. The neurostimulation system of claim 6, wherein the IPG is coated with Parylene.

9. A neurostimulation system for deep brain stimulation, the neurostimulation system comprising:

a burr hole plug comprising a cover and a base;
at least one deep brain stimulation (DBS) lead extending through an aperture defined through the base, the at least one DBS lead including at least one DBS electrode configured to apply stimulation to a subject;
an implantable pulse generator (IPG);
an extension electrically coupling the IPG to the at least one DBS lead;
an indifferent electrode positioned proximate the at least one DBS electrode to facilitate reducing an area between the indifferent electrode and the at least one DBS electrode;
the base including a metallic bottom, the metallic bottom comprising the indifferent electrode, with the Indifferent electrode being sized and shaped to facilitate preventing heating during application of radio frequency fields;
the at least one DBS lead including an indifferent ring and the base including at least one metallic clip with the metallic clip being configured to engage the indifferent ring such that the indifferent ring is electrically coupled to the metallic bottom; and
the at least one DBS lead including a connector pin positioned a fixed distance from the indifferent ring and at an extension connection between the at least one DBS lead and the extension.

10. The neurostimulation system of claim 9, wherein the at least one metallic clip is configured to engage the indifferent ring in a snap-fit engagement.

11. The neurostimulation system of claim 10, wherein the IPG is coated with Parylene.

* * * * *